United States Patent
Lauer et al.

(10) Patent No.: US 8,382,705 B2
(45) Date of Patent: Feb. 26, 2013

(54) CONVEYOR APPARATUS AND METHOD FOR SUPPLYING A MEDICINE-SOLUTION MIXTURE

(75) Inventors: Hans-Martin Lauer, München (DE); Matthias Wufka, München (DE); Sebastian Hörnig, Karlsfeld (DE); Doris Röthlein, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 315 days.

(21) Appl. No.: 12/681,183

(22) PCT Filed: Oct. 1, 2008

(86) PCT No.: PCT/EP2008/063125
§ 371 (c)(1),
(2), (4) Date: Aug. 20, 2010

(87) PCT Pub. No.: WO2009/047181
PCT Pub. Date: Apr. 16, 2009

(65) Prior Publication Data
US 2010/0318062 A1    Dec. 16, 2010

(30) Foreign Application Priority Data
Oct. 2, 2007   (DE) .......................... 10 2007 047 353

(51) Int. Cl.
*A61M 37/00* (2006.01)
(52) U.S. Cl. ......................................... 604/82; 604/518
(58) Field of Classification Search .............. 604/65–67, 604/82–92, 131, 151, 503, 518, 910; 600/365
See application file for complete search history.

(56) References Cited

U.S. PATENT DOCUMENTS 6,827,702 B2   12/2004   Lebel et al.
2003/0032867 A1   2/2003   Crothall et al.

FOREIGN PATENT DOCUMENTS

JP   2002-520718   7/2002

(Continued)

OTHER PUBLICATIONS

Translation of Office Action dated Apr. 4, 2012, for JP 2010-527436.

(Continued)

*Primary Examiner* — Theodore Stigell
(74) *Attorney, Agent, or Firm* — RatnerPrestia

(57) ABSTRACT

A conveyor apparatus and a method for supplying a medicine-solution mixture from a plurality of medicine-active ingredient solutions and additional solution constituents in a body by means of a plurality of feed devices is disclosed. The medicine-active ingredient solutions have different medicine-active ingredient parameters and constituents; the solution constituents have different parameters and constituents. The constituents of at least two medicine-active ingredient solutions and solution constituents are saved in at least one storage device; and are selected by means of one selection device for selection of at least one specific parameter and/or constituent of each medicine-active ingredient solution and/or the solution constituents. By means of a calculating device, at least one additional parameter from all selected parameters is calculated for the control and operation of at least one additional feed device for supplying at least one additional medicine-solution mixture to the body.

12 Claims, 1 Drawing Sheet

FOREIGN PATENT DOCUMENTS

| | | | |
|---|---|---|---|
| JP | 2006-519437 | | 8/2006 |
| WO | WO 00/03344 | | 1/2000 |
| WO | WO 2004/069095 | | 8/2004 |
| WO | WO2004/069095 | * | 8/2004 |
| WO | WO 2004/070546 | | 8/2004 |

OTHER PUBLICATIONS

Office Action dated Apr. 11, 2012, for CN 200880110497.5 with translation.
International Search Report, dated Jan. 16, 2009.
* cited by examiner

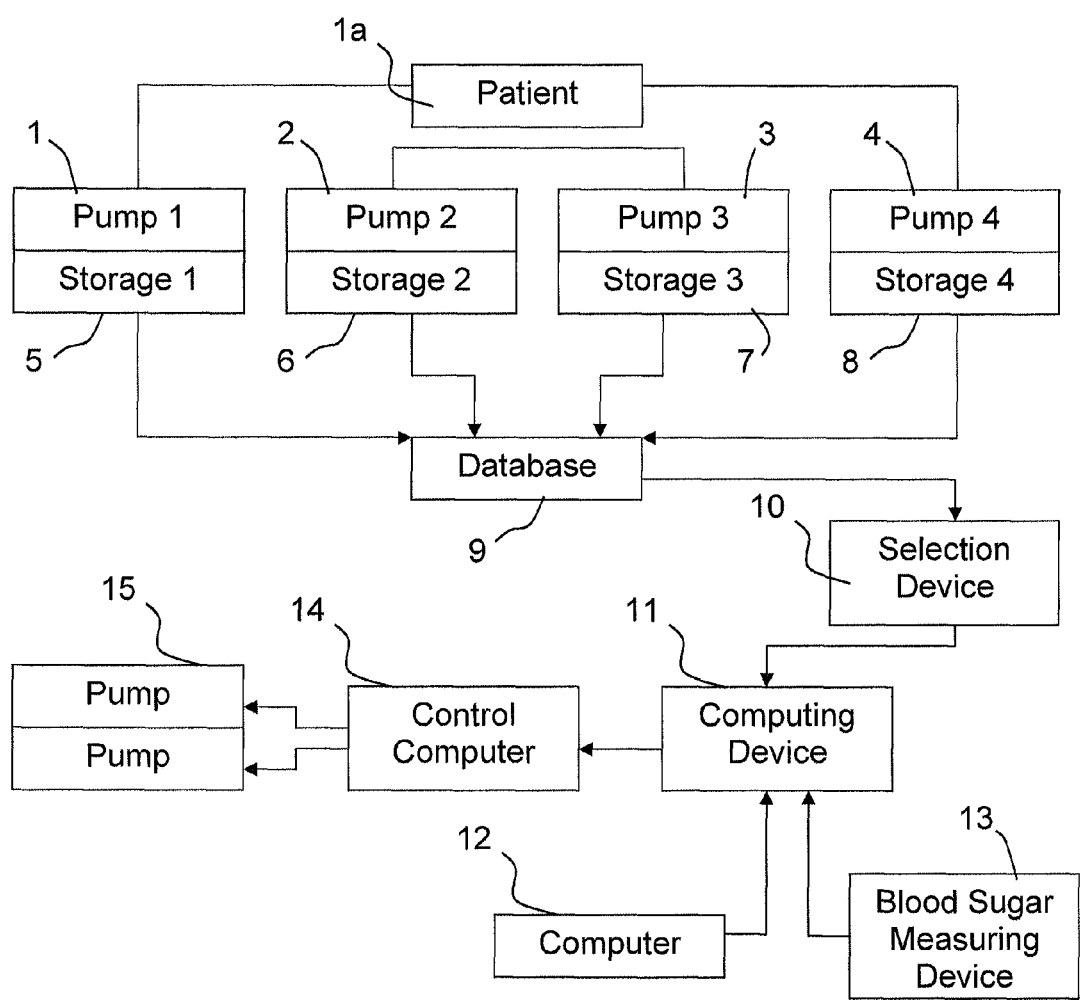

CONVEYOR APPARATUS AND METHOD FOR SUPPLYING A MEDICINE-SOLUTION MIXTURE

CROSS REFERENCE TO RELATED APPLICATIONS

This application is the U.S. national phase application of PCT International Application No. PCT/EP2008/063125, filed Oct. 1, 2008, which claims priority to German Patent Application No. DE 10 2007 047 353.4, filed Oct. 2, 2007, the contents of such applications being incorporated herein by reference.

FIELD OF THE INVENTION

The invention relates to a conveying device and a method for supplying a medicament solution mixture of a plurality of medicament active agent solutions and further solution constituents to the body by means of a plurality of feed units, wherein the medicament active agent solutions have different medicament active agent parameters and ingredients and the solution constituents have different parameters and ingredients, according to the preambles of patent claims 1 and 8.

BACKGROUND OF THE INVENTION

There are a number of known conveyor apparatus for supplying a medicament solution mixture to a body. For example, there are known apparatus having a plurality of infusion and/or syringe pumps, each of which supplies a solution having at least one specific active medicament ingredient to a body, as a result of which a medicament solution mixture is generated. In addition, further solution constituents are admixed as additives such as carrier solutions and preservatives, in order to achieve in this way a preservation of the medicament solution mixture and carrier substances for the transport of the active medicament ingredients.

Such infusion pump systems are often used with patients in need of intensive medical care. Here, the infusion pumps have the properties of supplying the medication in a continuously and accurately dosed manner. In order to achieve an optimised matching of the respective dosages provided by these pumps, the pumps are integrated in a common arrangement system, which usually comprises a central control unit, an operating unit and an alarm unit. As a result it becomes possible that even a two-digit number of various medicaments may be supplied to a body in such a way that they are matched to each other and are accurately dosed.

Such pumps have a delivery rate which is shown in terms of volume per time unit (1 ml/h). In comparison to this, in medicament a supplied medicament solution of the dose unit, for example in mg/kg body weight/24 h or mmol/min, is used. Therefore it is necessary to convert the dosage unit into a delivery rate for the pump, which is the job of the physician carrying out the treatment. To this end, the following formula applies:

$$\text{Rate} = \frac{\text{dose}}{\text{concentration of the medicament}}$$

Such a conversion is prone to calculation mistakes. Meanwhile, infusion pumps are being offered for this purpose, which allow a dosage unit to be input and which automatically convert this into a delivery rate. To this end, some additional technical features are necessary, such as for example the integration of a barcode scanner in order to scan a barcode attached by the pharmacy, in which the container which contains the medicament and which is to be inserted into the pump has been bought. This barcode contains information regarding the concentration of the active agent of the medicament contained in the syringe and regarding the type of medicament in question.

Upon scanning, the physician may input the desired dose for the selected medicament into the infusion pump by means of an input device, whereupon the pump will start the conversion of the dosage unit into the delivery rate and the administering of the medicament.

Both when indicating the concentration of the active agent and when inputting the dosage unit and converting into the delivery rate, so far only the main active agents of the medicament and thus of the medicament solution mixture have been considered and taken into account. This is often sufficient, provided only or predominantly a specific medicament is supposed to be administered.

Added to this is that when administering medicament by means of pumps, a calculation of the ratio between the liquid volumes supplied to the patient and the liquid volumes excreted by the patient is often carried out. As a result of such a calculation, information with regard to renal functions, different volume ratios and the rate of utilisation of the substances infused into the body may be obtained. Such ratio calculations which are automatically carried out by pumps rely on the fact that the volumes infused are determined and exclusively the main active agent is added up.

As a consequence, the present invention is based on the object of providing a conveyor apparatus and a method for supplying a medicament solution mixture of a plurality of medicament active agent solutions and further solution constituents, which enable(s) particularly in the area of artificial feeding the individual components of a medicament solution mixture for the subsequent calculation of parameters or values to be comprehensively taken into account.

SUMMARY OF THE INVENTION

In at least one aspect of the invention, in the case of a conveying apparatus for supplying a medicament solution mixture of a plurality of medicament active agent solutions having different medicament active agent parameters and ingredients and of further solution constituents having different parameters and ingredients, into a body by means of a plurality of feed devices, the parameters and/or ingredients of at least two, preferably of all of the medicament active agent solutions and solution constituents are stored in at least one storage device, a selection device for selecting at least one specific parameter and/or ingredient of each medicament active agent solution and/or the solution constituents is connected to the storage unit and a calculation unit for calculating at least one further parameter out of all of the selected parameters is connected to the selection unit for controlling the operation of at least one further feed device for supplying at least one further medicament solution mixture to the body.

In this way it becomes possible that a plurality of active agents with their associated parameters, such as for example the dosage, is taken into account for the subsequent calculation of the delivery rates or the volume-independent material volumes for setting up a ratio calculation, in order to obtain in this way an applicable and accurate delivery rate for the whole medicament solution mixture, which is often desired for the treatment of patients in order to achieve a combination effect as a result of the use of several medicaments, or an exact ratio calculation with regard to the incoming and outgoing volumes for taking into account the volumes of further medicaments with further active agents or with regard to the active agent volumes. This may advantageously lead to different medical decisions being taking for the treatment of a patient, because further medicaments are taken into account, than would be the case if only the main active agent had been taken into account in the calculations.

According to a preferred embodiment, the medicament solution mixture is a solution mixture for an artificial feeding with several nutrients. For the further solution constituents, carrier solutions are often used as the carrier material for the medicament active agents and preservatives for preserving the solutions. The ingredients may also be values for carbohydrates, proteins and fats, which are listed in nutrient tables often used for nutrient solutions.

In the case of such an artificial feeding, an automated administration of the nutrient solutions is carried out, wherein information with regard to the ingredients and their properties or parameters is stored comprehensively, i.e. for each nutrient solution and not just for the nutrient solution containing the main active agent, in a storage device or a database.

By selecting specific parameters such as, for example, the energy content (in kJ) for the individual nutrient solutions, it becomes possible to take into account the interdependencies of all the nutrient energy contents in the case of a plurality of administered nutrients for the calculation of an optimal delivery rate and in particular for the calculation of an insulin rate in the case of diabetes patients which lie on an intensive care unit and whose blood glucose level is also dependent on the type of artificial nourishment they receive and thus on their energy content. Thus, an automated calculation of a new insulin rate may be carried out as a function of all of the nutrient solutions and, of course, as a function of the blood glucose level to be measured and, if applicable, as a function of further patient-specific data such as weight, age and insulin sensitivity, on the basis of the process of administering the supplied nutrient energy contents as an input variable, without any further activities by a user or operator of the feed device according to the invention being required.

It is thus ensured that even if mixtures including several medicament active agents are used, an improved effect resulting from the sum of the active agents will be obtained, and it is not just the effect of the main active agent that is considered.

Advantageously, the energy which is additionally taken up as a side effect of the infusion of the medicament, such as for example in the case of medicaments dissolved in soya milk, may also be taken into account when indicating the nutrient energy contents as a parameter of the medicament active agent solutions or the nutrient solutions.

In order to determine the blood sugar level in a body, the calculation unit is connected to a blood sugar measuring device for measuring the blood sugar level and to an input unit for inputting body-specific data such as weight, age and insulin deficiency.

The artificial feeding used may be parenteral, enteral or a combination of the two.

The method according to at least one aspect of the invention for supplying the medicament solution mixture of a plurality of medicament active agent solutions and further solution constituents to a body by means of a plurality of feed units advantageously comprises the steps of storing the parameters and/or the ingredients of all of the medicament active agent solutions and solution constituents in at least one storage unit, selecting at least one specific parameter and/or ingredient from each medicament active agent solution and/or each solution constituent by means of a selection unit and calculating at least one further parameter from all of the selected parameters for the control of the operation of a further feed device by means of a calculation unit, in order to supply to the body as a result of this a further medicament solution mixture such as, for example, mixtures containing insulin.

During the selection of the nutrient energy amounts as a parameter of the nutrient solutions, the time curve of the supply of nutrient solutions by means of a plurality of infusion pumps is observed and included in the determination of a new insulin rate.

BRIEF DESCRIPTION OF THE DRAWINGS

Any advantages and expediencies can be taken from the following description in conjunction with the drawing.

FIG. 1 shows a schematic view of the individual components of the conveyor apparatus of the invention in accordance with an exemplary embodiment of the invention.

DETAILED DESCRIPTION OF THE PREFERRED EMBODIMENTS

FIG. 1 shows a schematic view of the conveyor apparatus according to the invention. For an enteral, artificial feeding of a patient 1a lying on an intensive care unit, a total of four infusion pumps 1-4 are arranged each with a storage unit 5-8, in order to feed the patient with nutrient solutions, associated carrier solutions and preservative solutions as well as, if applicable, further medicament solutions.

In the storage units 5-8, data with regard to the nutrient solutions and, if applicable, further medicament solutions containing the individual infusion pumps 1-4 are deposited. These may be, for example, parameters of the nutrient solutions, such as their energy content as a function of their ingredients, namely carbohydrates, proteins and fats. Of course, also the type of nutrient solution is stored therein.

This data is stored in a common database 9, so that it may be selected by operating personnel, with the same parameter, for example the energy content, being selected for all of the solutions.

Depending on the energy content, an operator will set an optimal delivery rate for the entire artificial feeding solution on each pump.

In a selection unit 10 the parameter, in this case the energy content, is selected.

In a calculation unit 11 a further parameter, in this case a new insulin rate, is calculated as a function of the time curve of the energies supplied to the patient as a function of all of the pumps 1-4.

For the calculation of the insulin rate, a current blood glucose value is additionally taken from the patient by means of a blood glucose measuring device 13 and is transferred to the calculation unit.

Moreover, by means of an input device 12, patient-specific data such as weight, age and insulin sensitivity are input, for example, by means of a keyboard, and are transferred to the calculation unit for the calculation of the new insulin rate.

Once the calculation unit has automatically calculated the new insulin rate on the basis of the data input and listed above, this is transferred as the result to a control calculation unit 14 which will then drive a further infusion pump 15 that is responsible for the supply of insulin to the patient 1a and will cause the supply of insulin.

The basic concept of the apparatus according to the invention and the method according to the invention is also applicable to the supply of any other medicament mixture having various active agents to a patient.

The invention claimed is:

1. A conveyor apparatus for supplying a medicament solution mixture of a plurality of medicament active agent solutions and/or solution constituents to a body, wherein the medicament active agent solutions and/or solution constituents have different medicament active agent parameters and/or ingredients, the conveyor apparatus comprising:
   a plurality of feed devices;
   at least one storage unit for storing the medicament active agent parameters and/or ingredients of at least two medicament active agent solutions and/or solution constituents being supplied by a corresponding at least two of the plurality of feed devices;
   a selection unit connected to the at least one storage unit for selecting at least one of the stored medicament active agent parameters and/or ingredients from each of the at least two medicament active agent solutions and/or solution constituents;
   a calculation unit for calculating at least one additional parameter based on the selected medicament active agent parameters and/or ingredients from each of the at least two medicament active agent solutions and/or solution constituents;
   a controller for controlling the operation of at least one other of the plurality of feed devices for supplying at least one additional medicament solution mixture to the body based on the calculated additional parameter.

2. The conveyor apparatus as claimed in claim 1, wherein the at least one additional medicament solution mixture is a solution mixture for an artificial feeding and the medicament active agent solutions are nutrient solutions.

3. The conveyor apparatus as claimed in claim 2, wherein the medicament active agent parameters are the nutrient energy content of the nutrient solution.

4. The conveyor apparatus as claimed in claim 2, wherein the artificial feeding used is parenteral, enteral or a combination of the two.

5. The conveyor apparatus as claimed in claim 1, wherein the solution constituents are carrier solutions and preservative solutions.

6. The conveyor apparatus as claimed in claim 1, wherein the ingredients are carbohydrates, proteins and fats.

7. The conveyor apparatus as claimed in claim 1, wherein the calculation unit is connected to a blood sugar measuring device for measuring the blood sugar level in the body and to an input device for inputting body-specific data.

8. A method for supplying a medicament solution mixture of a plurality of medicament active agent solutions and solution constituents to a body by means of a plurality of feed units, wherein the medicament active agent solutions have various medicament active agent parameters and ingredients and the solution constituents have various parameters and ingredients, comprising the steps of:
   storing the parameters and/or the ingredients of at least two medicament active agent solutions and solution constituents in at least one storage unit,
   selecting, at least one specific parameter and/or ingredient from each medicament active agent solution and/or the solution constituents by means of a selection unit, and
   calculating at least one additional parameter from all of the selected parameters for the control of the operation of at least one additional feed unit by means of a calculation unit, in order to supply at least one additional medicament solution mixture to the body.

9. The method as claimed in claim 8, wherein as a medicament solution mixture, a solution mixture for the artificial feeding is used, and as medicament active agent solutions, nutrient solutions having different nutrient energy contents are used as medicament active agent parameters.

10. The method as claimed in claim 9, wherein for the calculation of the additional parameter which is an insulin rate, body-specific data such as weight, age and insulin sensitivity of a patient, blood sugar level values of the patient as measured by means of an input device and by means of a blood sugar measuring device, as well as the nutrient energy contents and the time curve of the supply of the nutrient solutions by a plurality of infusion pumps are used.

11. The method as claimed in claim 9, wherein the artificial feeding used is parenteral, enteral or a combination of the two.

12. The method as claimed in claim 8 in that a warning indication is given in the case of an over- or underdosing of the supplied medicament solution mixture.

* * * * *

UNITED STATES PATENT AND TRADEMARK OFFICE
CERTIFICATE OF CORRECTION

PATENT NO. : 8,382,705 B2  Page 1 of 1
APPLICATION NO. : 12/681183
DATED : February 26, 2013
INVENTOR(S) : Lauer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 455 days.

Signed and Sealed this
First Day of September, 2015

Michelle K. Lee
*Director of the United States Patent and Trademark Office*